United States Patent
Akagane

(10) Patent No.: US 10,064,641 B2
(45) Date of Patent: Sep. 4, 2018

(54) ULTRASONIC PROBE AND ULTRASONIC TREATMENT INSTRUMENT

(71) Applicant: OLYMPUS CORPORATION, Hachioji-shi, Tokyo (JP)

(72) Inventor: Tsunetaka Akagane, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/265,959

(22) Filed: Sep. 15, 2016

(65) Prior Publication Data
US 2017/0000514 A1    Jan. 5, 2017

Related U.S. Application Data

(63) Continuation of application No. PCT/JP2015/068335, filed on Jun. 25, 2015.

(30) Foreign Application Priority Data

Jul. 10, 2014 (JP) ................................. 2014-142630

(51) Int. Cl.
*A61B 17/32* (2006.01)
*A61B 18/00* (2006.01)
*A61N 7/00* (2006.01)

(52) U.S. Cl.
CPC ...... *A61B 17/320068* (2013.01); *A61B 18/00* (2013.01); *A61N 7/00* (2013.01);
(Continued)

(58) Field of Classification Search
CPC ........... A61B 17/320068–2017/320098; A61B 17/22012–2017/22025;
(Continued)

(56) References Cited

U.S. PATENT DOCUMENTS

2013/0116686 A1* 5/2013 Akagane ............ A61B 18/1442
606/41
2015/0045701 A1    2/2015 Akagane

FOREIGN PATENT DOCUMENTS

CN    103354736 A    10/2013
EP    2 898 845 A1    7/2015
(Continued)

OTHER PUBLICATIONS

Sep. 29, 2015 International Search Report issued in Patent Application No. PCT/JP2015/068335.
(Continued)

*Primary Examiner* — Ryan J Severson
*Assistant Examiner* — Charles Wei
(74) *Attorney, Agent, or Firm* — Oliff PLC

(57) ABSTRACT

An ultrasonic probe includes a hook curved relative to a probe main body in a first perpendicular direction and forming a part of a distal surface, and a first base surface extending toward a proximal direction from a hook proximal end and serving as a base plane of the hook. The ultrasonic probe includes a protrusion protruding toward a second perpendicular direction with a second base surface, which is directed in a second perpendicular direction opposite to the first perpendicular direction, being as a base plane and extending toward both the proximal direction and a distal direction from a reference position located on a section, which passes through the hook proximal end and which is perpendicular to a longitudinal axis.

7 Claims, 5 Drawing Sheets

(52) U.S. Cl.
CPC ............ *A61B 2017/320078* (2017.08); *A61B 2017/320098* (2017.08)

(58) Field of Classification Search
CPC .. A61B 17/22004–2017/22011; A61B 17/225; A61B 18/0206; A61F 9/00745; A61C 3/03; A61C 1/07
See application file for complete search history.

(56) References Cited

FOREIGN PATENT DOCUMENTS

| | | |
|---|---|---|
| JP | H08-503621 A | 4/1996 |
| JP | 2007-054665 A | 3/2007 |
| JP | 2010-522034 A | 7/2010 |
| JP | 5555392 B1 | 7/2014 |
| WO | 2014/045667 A1 | 3/2014 |

OTHER PUBLICATIONS

Jan. 19, 2017 International Preliminary Report on Patentability.
Feb. 23, 2018 Office Action issued in Chinese Application No. 201580017413.3.
Mar. 2, 2018 Extended Search Report issued in European Application No. 15819625.3.

\* cited by examiner

ULTRASONIC PROBE AND ULTRASONIC TREATMENT INSTRUMENT

CROSS-REFERENCE TO RELATED APPLICATIONS

This is a Continuation Application of PCT Application No. PCT/JP2015/068335, filed Jun. 25, 2015 and based upon and claiming the benefit of priority from prior Japanese Patent Application No. 2014-142630, filed Jul. 10, 2014, the entire contents of which are incorporated herein by reference.

BACKGROUND OF THE INVENTION

1. Field of the Invention

The present invention relates to an ultrasonic probe that enables an ultrasonic vibration to be transmitted from a proximal direction toward a distal direction, and an ultrasonic treatment instrument including the ultrasonic probe.

2. Description of the Related Art

Jpn. PCT National Publication No. 2010-522034 discloses an ultrasonic treatment instrument including an ultrasonic probe that enables an ultrasonic vibration to be transmitted from a proximal direction toward a distal direction. A distal treatment section configured to treat a treated target (such as a living tissue) using the transmitted ultrasonic vibration, is provided in the distal portion of the ultrasonic probe. In the distal treatment section, a hook which protrudes toward a direction perpendicular to a longitudinal axis (a first perpendicular direction) is formed. The hook forms part of a distal surface of the ultrasonic probe. In the state where the treated target is caught by the hook from the proximal side, the ultrasonic probe (treatment section) is vibrated due to the ultrasonic vibration, with the result that the treated target caught by the hook is resected. In the state where the ultrasonic vibration is transmitted, the ultrasonic probe performs longitudinal vibration whose vibration direction is parallel to the longitudinal axis.

BRIEF SUMMARY OF THE INVENTION

According to one aspect of the invention, an ultrasonic probe having a longitudinal axis, the ultrasonic probe including: a probe main portion extending along the longitudinal axis, and configured to transmit an ultrasonic vibration from a proximal direction toward a distal direction; a hook provided on a distal direction side with respect to the probe main portion, and curved relative to the probe main body in a first perpendicular direction, which is one of directions perpendicular to the longitudinal axis, the hook forming a part of a distal surface of the ultrasonic probe; a first base surface provided in a part of an outer surface portion directed in the first perpendicular direction, and serving as a base plane of the hook protruding toward the first perpendicular direction, the first base surface extending toward the proximal direction from a hook proximal end, which is a boundary position between a root of the hook and the base plane, the first base surface being away from the longitudinal axis toward the first perpendicular direction by a distance which is constant at a predetermined dimension over an entire length of the first base surface in a longitudinal direction along the longitudinal axis; a second base surface provided in a part of the outer surface portion directed in a second perpendicular direction opposite to the first perpendicular direction; and a protrusion continuous with the distal direction side of the second base surface, and protruding toward the second perpendicular direction with the second base surface being as a base plane, the protrusion extending toward both the proximal direction and the distal direction from a reference position located on a section, which passes through the hook proximal end of the hook and which is perpendicular to the longitudinal axis.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

First Embodiment

The first embodiment of the present invention will be described with reference to FIGS. 1 to 7.

Figure 1:
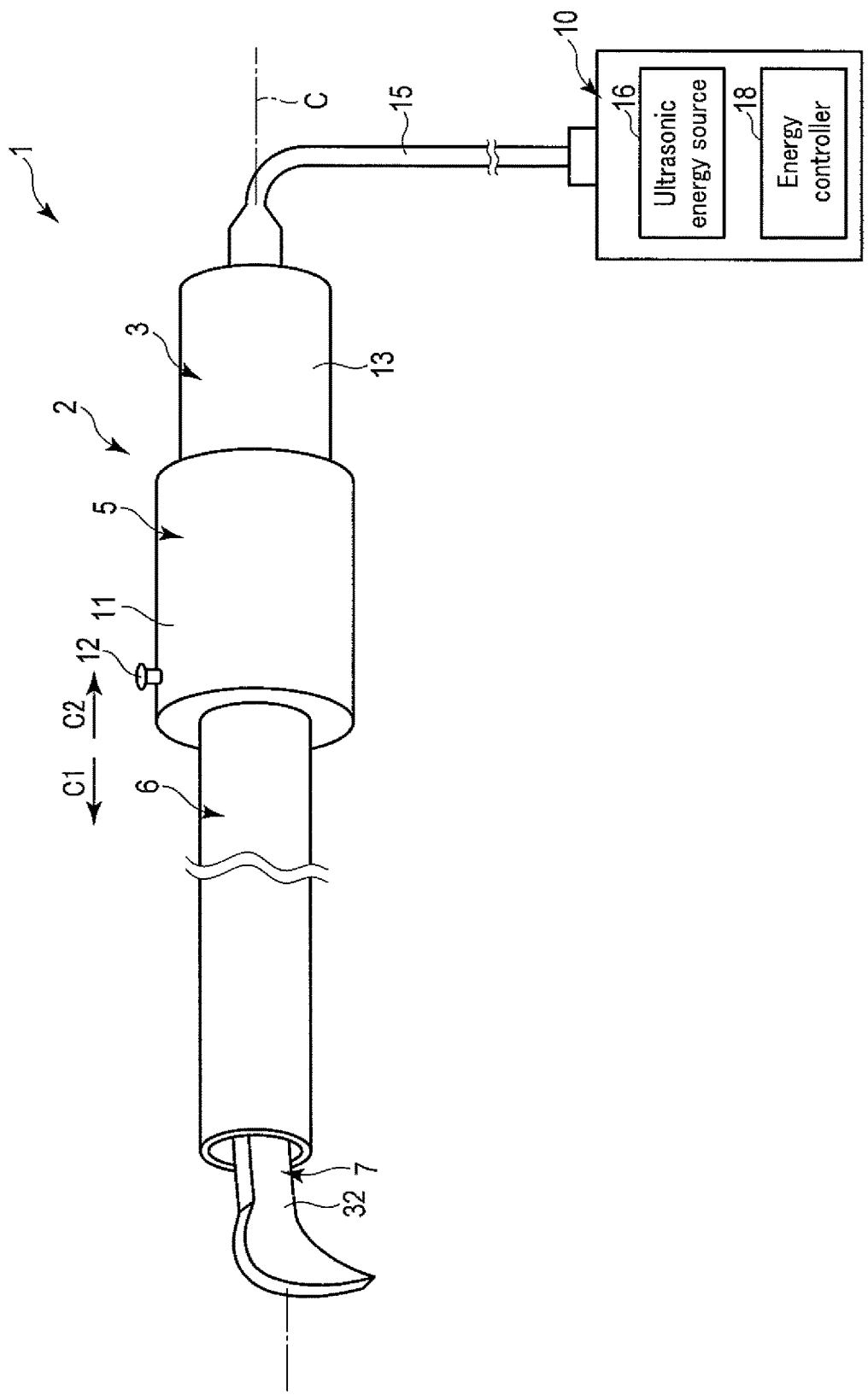
FIG. 1 is a schematic view showing an ultrasonic treatment system according to a first embodiment.

FIG. 1 shows an ultrasonic treatment system (ultrasonic treatment apparatus) 1 of the present embodiment. As shown in FIG. 1, the ultrasonic treatment system 1 includes an ultrasonic treatment instrument 2. The ultrasonic treatment instrument 2 has a longitudinal axis C. One direction parallel to the longitudinal axis C is defined as a distal direction (indicated by arrow C1 in FIG. 1), and the other direction opposite to the distal direction is defined as a proximal direction (indicated by arrow C2 in FIG. 1). The two directions (distal direction and proximal direction) parallel to the longitudinal axis C (along the longitudinal axis C) are collectively referred to as a longitudinal direction.

The ultrasonic treatment instrument 2 includes a transducer unit 3, a holding unit 5, a sheath 6, and an ultrasonic probe 7. The holding unit 5 includes a tubular case portion 11 extending along the longitudinal axis C. An energy operation input button 12, which is an energy operation input section, is attached to the tubular case portion 11.

The transducer unit 3 includes a transducer case 13. The oscillator unit 3 is coupled to the holding unit 5 by inserting the transducer case 13 from the proximal direction side into the tubular case portion 11. A proximal portion of the transducer case 13 is connected to one end of a cable 15. The other end of the cable 15 is connected to an energy source unit 10. The energy source unit 10 includes an ultrasonic energy source (ultrasonic electric power source) 16 and an energy controller 18. The energy source unit 10 is, for example, an energy generator (electric power generator), and the ultrasonic energy source 16 is, for example, a power source provided in the energy generator.

The energy controller 18 is provided in the energy generator, for example, and is constituted of a processor including a central processing unit (CPU) or an application specific integrated circuit (ASIC). Inside the tubular case portion 11, a switch (not shown) is provided. The energy controller 18 is electrically connected to a switch via a signal path (not shown) extending though the oscillator case 13 and an inside of the cable 15. When an energy operation is input in the energy operation input button 12, the switch becomes ON, and an operation signal is transmitted to the energy controller 18 by way of the signal path. Based on the transmitted operation signal, the energy controller 18 controls the output state of the ultrasonic generating energy (ultrasonic generating electric power) output from the ultrasonic energy source 16.

Figure 2:
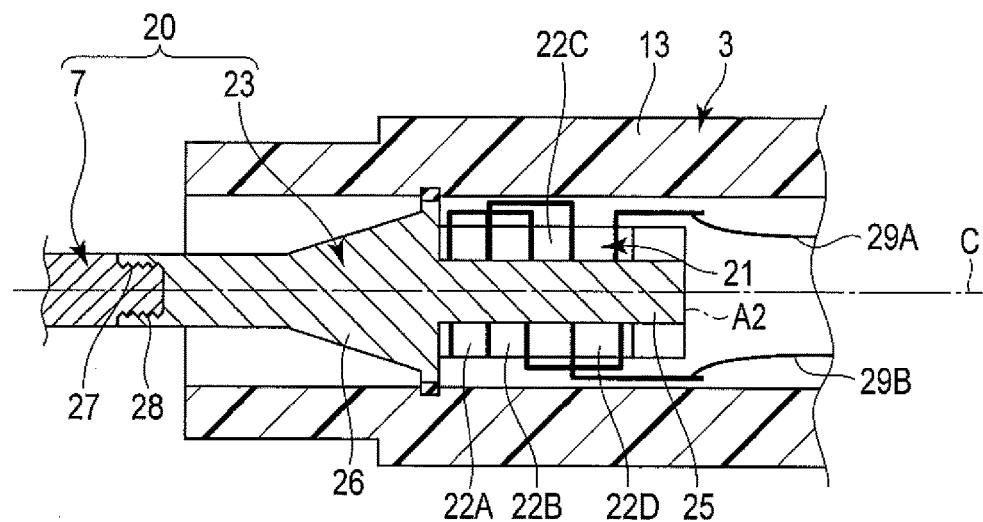
FIG. 2 is a cross-sectional view schematically showing a configuration of a transducer unit according to the first embodiment.

FIG. 2 shows a configuration of the transducer unit 3. As shown in FIG. 2, the transducer unit 3 includes the aforementioned transducer case 13, and an ultrasonic transducer 21 which is a vibration generator provided inside the transducer case 13. The ultrasonic oscillator 21 includes a plurality of (four in the present embodiment) piezoelectric elements 22A-22D, which convert a current (alternating current) into an ultrasonic vibration. Supplied with the ultrasonic generating energy (ultrasonic generating electric power), the ultrasonic transducer 21 generates the ultrasonic vibration.

Inside the transducer case 13, a horn member 23 extends along the longitudinal axis C. The horn member 23 includes a transducer mount 25. Members forming the ultrasonic transducer 21, such as piezoelectric elements 22A-22D, are mounted on the transducer mount 25. The horn member 23 includes a cross-sectional area change portion 26. The cross sectional area of the cross-sectional area change portion 26, which is taken perpendicularly to the longitudinal axis C, decreases toward the distal direction. The cross-sectional area change portion 26 increases the amplitude of the ultrasonic vibration. An internal thread portion 27 is provided in a distal portion of the horn member 23.

As shown in FIG. 2, an external thread portion 28 is provided in a proximal portion of the ultrasonic probe 7. The internal thread portion 27 and the external thread portion 28 are screwed together, and the ultrasonic probe 7 is connected to the distal direction side of the horn member 23. The ultrasonic probe 7 extends along the longitudinal axis C. The horn member 23 is connected to the ultrasonic probe 7 inside the tubular case portion 11. The ultrasonic transducer 21, which is a vibration generator, is located on the proximal direction side with respect to the ultrasonic probe 7.

As shown in FIG. 1, the sheath 6 is coupled to the holding unit 5 when it is inserted into the tubular case portion 11 from the distal direction side. Inside the tubular case portion 11, the sheath 6 is coupled to the transducer case 13. The ultrasonic probe 7 is inserted through the sheath 6. Thus, the distal portion of the ultrasonic probe 7 protrudes from the distal end of the sheath 6 toward the distal direction.

As shown in FIG. 2, each of electric lines 29A and 29S is connected, at one end, to the ultrasonic transducer 21. The electric lines 29A and 29B extend through the inside of the cable 15, and at the other end, each of the electric lines 29A and 29S is connected to the ultrasonic energy source 16 of the control unit 10. When the ultrasonic generating electric power is supplied to the ultrasonic transducer 21 from the ultrasonic energy source 16 via the electric lines 29A and 29B, the ultrasonic vibration is generated in the ultrasonic transducer 21. The generated ultrasonic vibration is transmitted from the ultrasonic transducer 21 via the horn member 23 to the ultrasonic probe 7. The horn member 23 and the ultrasonic probe 7 form an vibration transmission unit 20, which transmits the ultrasonic vibration generated by the ultrasonic transducer 21 from the proximal direction toward the distal direction.

When the ultrasonic vibration generated by the ultrasonic transducer 21 is transmitted, the vibration transmission unit 20 vibrates in a predetermined vibration mode (vibration condition) used at the time of treatment. In the predetermined vibration mode, the vibration transmission unit 20 performs longitudinal vibration, the vibrating direction of which is parallel to the longitudinal axis C (longitudinal direction). In the established vibration mode, the distal end of the vibration transmission unit 20 (the distal end of the ultrasonic probe 7) and the proximal end of the vibration transmission unit 20 (the proximal end of the horn member 23) are antinode positions of the longitudinal vibration. Antinode position A1, which is located at the distal end of the vibration transmission unit 20, is located most distally among the antinode positions of the longitudinal vibration. Antinode position A2, which is located at the proximal end of the vibration transmission unit 20, is located most proximally among the antinode positions of the longitudinal vibration. In the predetermined vibration mode, the number of antinode positions in the longitudinal vibration and the number of node positions in the longitudinal vibration are fixed between the distal end of the vibration transmission unit 20 and the proximal end of the vibration transmission unit 20. At least one node position in the longitudinal vibration is present between the distal end of the vibration transmission unit 20 and the proximal end of the vibration transmission unit 20. The energy controller 18 adjusts the frequency of the current (AC current) supplied to the ultrasonic transducer 21, so that the resonant frequency of the vibration transmission unit 20 is adjusted and the vibration transmission unit 20 performs the longitudinal vibration in the predetermined vibration mode. The predetermined vibration mode (namely, the number of node positions and the number of antinode positions in the longitudinal vibration) is determined in accordance with the longitudinal dimension of the vibration transmission unit 20 to be employed, the resonance frequency of the longitudinal vibration used for treatment, etc.

Figure 3:
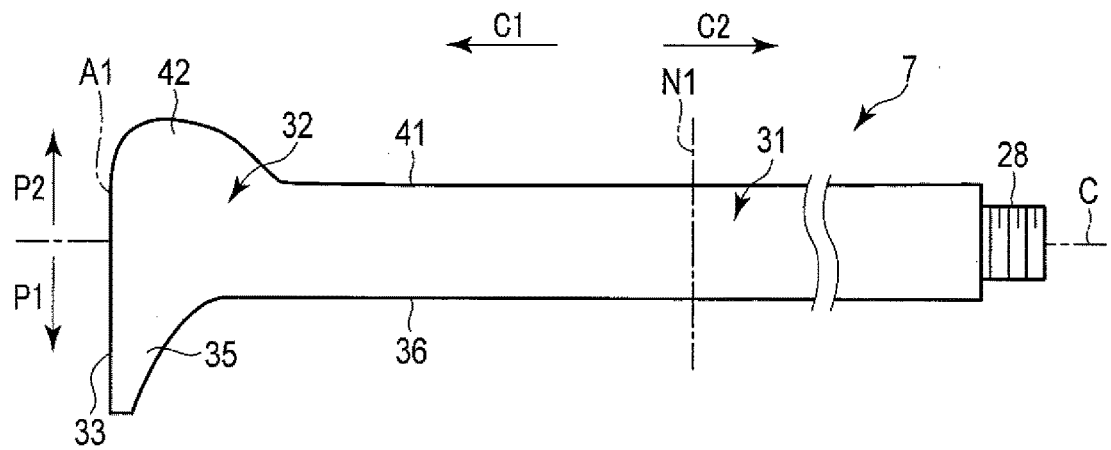
FIG. 3 is a side view schematically showing a configuration of an ultrasonic probe according to the first embodiment.
Figure 4:
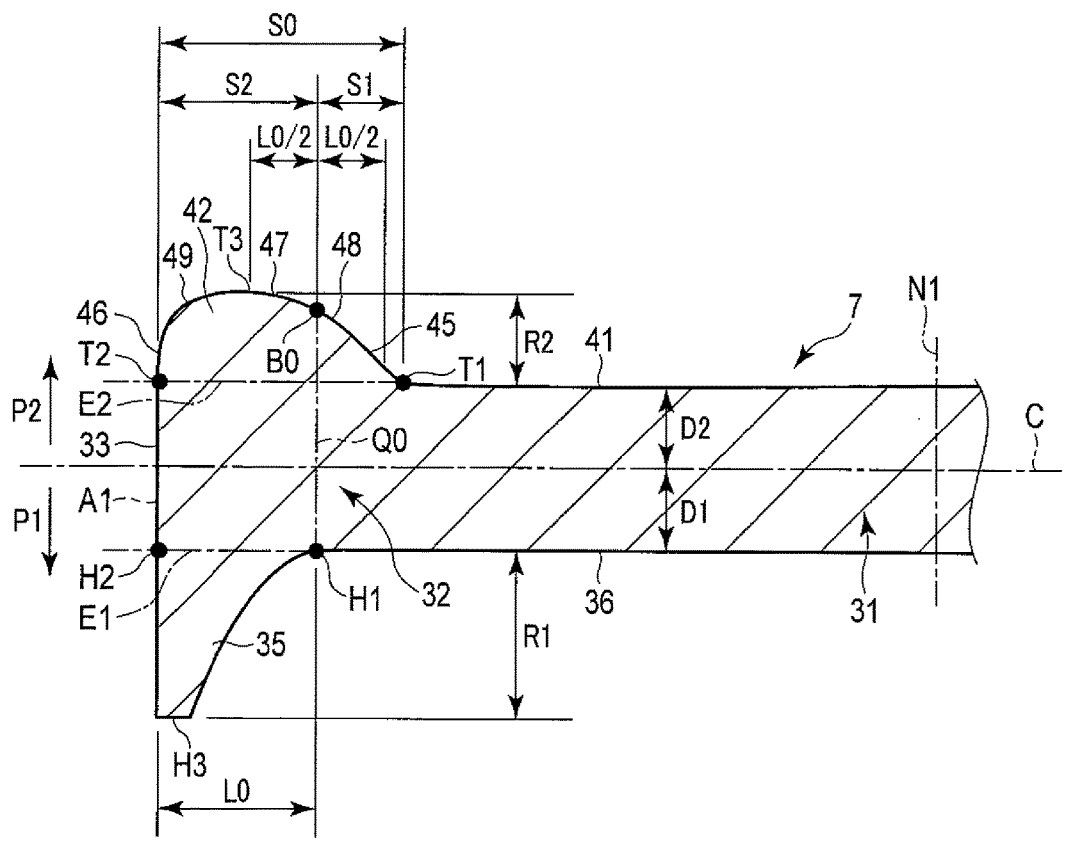
FIG. 4 is a cross-sectional view schematically showing a configuration of a distal portion of the ultrasonic probe according to the first embodiment.

FIG. 3 shows the ultrasonic probe 7. FIG. 4 shows the distal portion of the ultrasonic probe 7 in an enlarged scale. One of the directions perpendicular to the longitudinal axis C (and intersecting therewith) is defined as a first perpendicular direction (indicated by arrow 21 in FIGS. 3 and 4), and the direction opposite to the first perpendicular direction is defined as a second perpendicular direction (indicated by arrow P2 in FIGS. 3 and 4). One of the two directions perpendicular to the longitudinal axis C and also perpendicular to both the first and second perpendicular directions is defined as a third perpendicular direction (the direction perpendicular to the drawing sheets of FIGS. 3 and 4 and being vertically upward from the horizontally placed drawing sheets), and the direction opposite to the third perpendicular direction is defined as a fourth perpendicular direction (the direction perpendicular to the drawing sheets of FIGS. 3 and 4 and being vertically downward from the horizontally placed drawing sheets). FIG. 3 shows the ultrasonic probe 7 viewed from a third perpendicular direction side, and FIG. 4 shows a cross section that is perpendicular to both the third and fourth perpendicular directions.

As shown in FIGS. 3 and 4, the ultrasonic probe 7 includes a probe main portion 31 extending along the longitudinal axis C. The ultrasonic vibration transmitted to the ultrasonic probe 7 is transmitted through the probe main portion 31 from the proximal direction toward the distal direction. The longitudinal axis C of the ultrasonic treatment instrument 2 is the same as the central axis of the probe main portion 31. Therefore, the ultrasonic probe 7 has longitudinal axis C which is the central axis of the probe main portion 31. The ultrasonic probe 7 is provided with a distal treatment section 32 located on the distal direction side with respect to the probe main portion 31. The distal treatment section 32 treats a treated target, such as a living tissue, using the ultrasonic vibration transmitted through the probe main portion 31. The distal treatment section 32 forms a distal surface 33 of the ultrasonic probe 7 (vibration transmission unit 20). The ultrasonic probe 7 is inserted through the sheath 6, with the distal treatment section 32 protruding from the distal end of the sheath toward the distal direction.

As described above, in the predetermined vibration mode, antinode position A1 of the longitudinal vibration is located on the distal surface 33. Among the nodes of the longitudinal vibration in the predetermined vibration mode, node position N1 located most distally is defined. In the established vibration mode, the node position N1 is located on the proximal direction side with respect to the distal treatment section 32, and is located within the probe main portion 31. Therefore, the node position N1 of the longitudinal vibration is located inside the sheath 6.

The distal treatment section 32, which is located on the distal direction side with respect to the probe main portion 31, is provided with a hook 35. The hook 35 is curved in the first perpendicular direction relative to the probe main portion 31 (longitudinal axis C). The hook 35 protrudes toward the first perpendicular direction in the distal treatment section 32. The hook 35 forms part of the distal surface 33 of the ultrasonic probe 7. Provided with the hook 35 protruding toward the first perpendicular direction, the ultrasonic probe 7 has a substantially "L" shape.

On the outer surface of the ultrasonic probe 7, a first base surface 36, which is a reference surface directed in the first perpendicular direction, is provided. In other words, the first base surface 36 is provided in part of an outer surface of the ultrasonic probe 7 facing the first perpendicular direction. The first base surface 36 is located on the first perpendicular direction side with respect to the longitudinal axis C. The hook 35 protrudes toward the first perpendicular direction, with the first base surface 36 as a base surface. Therefore, that portion of the distal treatment section 32 which protrudes in the first perpendicular direction (located on the first perpendicular direction side) from the first base surface 36 is the hook 35. An extension plane E1, which is an extension of the first base surface 36 in the distal direction, is a base section of the hook 35 (a hook root section) from which the hook 35 protrudes.

The first base surface 36 extends in the proximal direction from a hook proximal end H1, which is the proximal end of the hook 35. The hook proximal end H1 is a curve start position (a hook start position) at which the hook 35 starts curving in the first perpendicular direction, and is also a boundary position between the hook 35 and the first base surface 36. In the present embodiment, the first base surface 36 extends through the outer surface of the probe main portion 31. In other words, part of the outer surface of the probe main portion 31 (namely, a part the outer surface portion directed in the first perpendicular direction) is defined by the first base surface 36, and this first base surface 36 extends from the hook proximal end H1 (distal treatment section 32) to the probe main portion 31.

A hook distal end H2, which is the distal end of the hook 35, is located on the distal surface 33 of the ultrasonic probe 7. The hook 35 has a reference dimension L0 which is a dimension in the longitudinal direction between the hook proximal end H1 and the hook distal end H2. The reference dimension L0 is a dimension representing the longitudinal dimension of the hook 35 (hook base dimension), as measured in the extension plane E1, i.e., the root section of the hook 35. Therefore, the hook proximal end H1 is a proximal position of the base section (E1) from which the hook 35 protrudes in the first perpendicular direction. In other words, the hook proximal end R1 is a boundary position between the root portion of the protrusion of the hook 35 and the first base surface (base plane) 36.

The distance (first surface distance) D1 by which the first base surface 36 is away from the longitudinal axis C in the first perpendicular direction is constant (uniform) within a predetermined dimensional range (predetermined dimension) over the entire length of the first base surface 36 in the longitudinal direction. When the ultrasonic probe 7 is designed and manufactured, the distance D1 between the longitudinal axis C and the first base surface 36 should be equal in the longitudinal direction over the entire length of the first base surface 36. In the actual design and manufacture, however, the distance D1 may not be exactly the same over the entire length of the first base surface 36 due to error; it may be slightly vary. Therefore, a case where the distance D1 slightly varies due to the error in the designing or manufacturing process in addition to a case where the distance D1 is equal over the entire length is included in a case where the distance D1 by which the first base surface 36 is away from the longitudinal axis C in the first perpendicular direction is constant (uniform) within the predetermined range. That is, even where the distance D1 from the longitudinal axis C does not vary more than a predetermined range over the entire length, the distance D1 by which the first base surface 36 is away from the longitudinal axis C is considered uniform within the predetermined dimensional range. Therefore, as long as the distance D1 by which the first base surface 36 is away from the longitudinal axis C in the first perpendicular direction varies within ±0.1 mm over the entire length, the distance D1 from the longitudinal axis C is regarded as being constant (uniform) within the predetermined dimensional range.

On the outer surface of the ultrasonic probe 7, a second base surface 41, which is a reference surface directed in the second perpendicular direction opposite to the first perpendicular direction, is provided. In other words, the second base surface 41 is provided in part of an outer surface of the ultrasonic probe 7 facing the second perpendicular direction. The second base surface 41 is located on the second perpendicular direction side with respect to the longitudinal axis C. The second base surface 41 extends from the distal treatment section 32 toward the proximal direction. In the present embodiment, the second base surface 41 extends through the outer surface of the probe main portion 31. In other words, part of the outer surface of the probe main portion 31 (namely, a part of the outer surface portion directed in the second perpendicular direction) is defined by the second base surface 41, and this second base surface 41 extends from the distal treatment section 32 to the probe main portion 31.

The distance (second surface distance) D2 by which the second base surface 41 is away from the longitudinal axis C in the second perpendicular direction is constant (uniform) within a predetermined dimensional range over the entire length of the second base surface 41 in the longitudinal direction. Here, a case where the distance D2 slightly varies due to the error in the designing or manufacturing process in addition to a case where the distance D2 is equal over the entire length is included in a case where the distance D2 by which the second base surface 41 is away from the longitudinal axis C in the second perpendicular direction is constant within the predetermined range. That is, even where the distance D2 from the longitudinal axis C does not vary more than a predetermined range over the entire length, the distance D2 by which the second base surface 41 is away from the longitudinal axis C is considered uniform within the predetermined dimensional range. Therefore, as long as the distance D2 by which the second base surface 41 is away from the longitudinal axis C in the second perpendicular direction varies within ±0.1 mm over the entire length, the distance D2 from the longitudinal axis C is regarded as being constant (uniform) within the predetermined dimensional range.

The distal treatment section 32 is provided with a protrusion 42 protruding toward the second perpendicular direction, with the second base surface 41 being as a base surface. Therefore, that portion of the distal treatment section 32 which protrudes in the second perpendicular direction (is located on the second perpendicular direction side) from the second base surface 41 is the protrusion 42. The protrusion 42 is continuous with the distal direction side of the second base surface 41. The second base surface 41 extends toward the proximal direction from a protrusion proximal end T1, which is the proximal end of the protrusion 42. The protrusion proximal end T1 of the protrusion 42 is a boundary position between the protrusion 42 and the second base surface 41. The protrusion 42 is located at an angular position approximately 180° away from the hook 35 around the longitudinal axis C. In the present embodiment, an extension plane E2, which is an extension of the second base surface 41 in the distal direction, is a base section of the protrusion 42 (a protrusion root section) from which the protrusion 42 protrudes.

In the present embodiment, the protrusion 42 forms part of the distal surface 33 of the ultrasonic probe 7. Therefore, a protrusion distal end T2, which is the distal end of the protrusion 42, is located on the distal surface 33 of the ultrasonic probe 7. The protrusion 42 has a protrusion width dimension S0, which is a dimension between the protrusion proximal end T1 and the protrusion distal end T2 in the longitudinal direction. The protrusion width dimension S0 is a dimension representing the longitudinal dimension of the protrusion 42 (protrusion base dimension), as measured in the extension plane E2, i.e., the root section of the hook 42.

A section which passes the hook proximal end H1 of the hook 35 and is perpendicular to the longitudinal direction C is defined as a reference section Q0. The protrusion 42 extends toward the distal direction and the proximal direction from reference position B0 located on the reference section Q0. In other words, the projection 42 extends through the reference position B0. Therefore, the protrusion proximal end T1, which is the proximal position of the protrusion 42, is located on the proximal direction side with respect to the hook proximal end (hook start position) H1 of the hook 35, and the protrusion distal end T2, which is the distal end position of the projection 42, is located on the distal direction side with respect to the hook proximal end H1 of the hook 35. On the reference section Q0, the reference position B0 of the protrusion 42 is located at an angular position approximately 180° away from the hook proximal end H1.

The protrusion 42 has a first extension dimension (first protrusion extension dimension) S1 toward the proximal direction from the reference position B0 to the protrusion proximal end T1. The first extension dimension S1 is more than half of the reference dimension (hook base dimension) L0 of the hook 35, which represents how the hook proximal end H1 and the hook distal end H2 are away from each other in the longitudinal direction. In other words, the protrusion 42 extends in the proximal direction from the reference position B0 by the first extension dimension S1, which is more than half (L0/2) of the reference dimension L0. The protrusion 42 has a second extension dimension (second protrusion extension dimension) S2 from the reference position B0 to the protrusion distal end T2 toward the distal direction. The second extension dimension S2 is more than half of the reference dimension (hook root dimension) L0 of the hook 35, which represents a dimension between the hook proximal end H1 and the hook distal end H2 in the longitudinal direction. In other words, the protrusion 42 extends in the distal direction from the reference position B0 by the second extension dimension S2, which is more than half (L0/2) of the reference dimension L0. Since each of the first extension dimension S1 and the second extension dimension S2 is more than half (L0/2) of the reference dimension L0, the projection width dimension S0 of the projection 42 is more than the reference dimension L0 of the hook 35.

The dimension from the first base surface 36 (extension plane E1) to the hook protruding end E3, which is the protruding end of the hook 35, in the first perpendicular direction will be referred to as a first protruding dimension (hook protruding dimension) R1. The dimension from the second base surface 41 (extension plane E2) to the protrusion protruding end T3, which is the protruding end of the protrusion 42, in the second perpendicular direction will be referred to as a second protruding dimension (protrusion protruding dimension) R2. The first protruding dimension R1 is larger than the second protruding dimension R2.

On the outer surface of the protrusion 42, a proximal-side protrusion surface 45 directed in the proximal direction and a distal-side protrusion surface 46 directed in the distal direction are provided. The proximal-side protrusion surface 45 extends in the second perpendicular direction from the protrusion proximal end T1, which is a boundary position between the protrusion 42 and the second base surface 41. The distal-side protrusion surface 46 extends in the second perpendicular direction from the protrusion distal end T2. The distal-side protrusion surface 46 forms part of the distal surface 33 of the ultrasonic probe 7. On the outer surface of the protrusion 42, a protrusion end surface 47 forming a protrusion protruding end T3, which is the protruding end of the protrusion 42, is provided. The protruding end surface 47 faces the second perpendicular direction.

Further, on the outer surface of the protrusion 42, a proximal-side curved surface 48 is continuous between the proximal-side protrusion surface 45 and the protrusion end surface 47, and a distal-side curved surface 49 is continuous between the distal-side protrusion surface 46 and the protrusion end surface 47. The proximal-side curved surface 48 and the distal-side curved surface 49 are arcuate curved surfaces in a plane perpendicular to the third and fourth perpendicular directions. Therefore, the proximal-side curved surface 48 and the distal-side curved surface 49 are arcuate, when viewed from each of the third perpendicular direction and the fourth perpendicular direction.

Next, the function and advantage of the ultrasonic probe 7 and the ultrasonic treatment instrument 2 according to the present embodiment will be described. When a treated target such as a body tissue (blood vessel) is treated by the ultrasonic treatment system 1, the ultrasonic probe 7 and the sheath 6 are inserted into a body cavity. The treated target is caught with the hook 35 of the distal treatment section 32. The treated target comes into contact with the hook 35 from the proximal direction. With the treated target caught with the hook 35 from the proximal direction, an energy operation is input with the energy operation input button 12. As a result, the energy controller 18 controls the ultrasonic energy source 16 to output ultrasonic generating energy (ultrasonic generating electric power).

Supplied with the ultrasonic generating energy (alternating current), the ultrasonic transducer 21 generates an ultrasonic vibration. The generated ultrasonic vibration is transmitted to the ultrasonic probe 7 via the horn member 23. In the ultrasonic probe 7 (probe main portion 31), the ultrasonic vibration is transmitted toward the distal direction to the distal treatment section 32, and the vibration transmission unit 20 (including the ultrasonic probe 7) longitudinally vibrates. When the distal treatment section 32 performs longitudinal vibration, a vibrating direction of which is parallel to the longitudinal axis C, with the treated target being caught with the hook 35, the treatment target caught with the hook 35 is cut.

In the treatment, high-frequency electric power (high-frequency current) may be supplied to the distal treatment section 32, together with the ultrasonic vibration. In this case, the energy source unit 10 is provided with an energy source (e.g., an electric power source) different from the ultrasonic energy source 16, and high-frequency electric power (high-frequency energy) is output from that energy source. The out high-frequency power is supplied, by way of a electric line different (not shown) from electric lines 29A and 29B extending inside the cable 15, the horn member 23 and the ultrasonic probe 7, to the distal treatment section 32. In addition, the energy source supplies the high-frequency power electrode plate (not shown) arranged outside the body. As a result, a high-frequency current flows between the hook 35 and the electrode plate outside the body, and the high-frequency current flows to the treated target caught with the hook 35. Thus, the treated object is coagulated (sealed) simultaneous with the incision (cutting).

Figure 5:
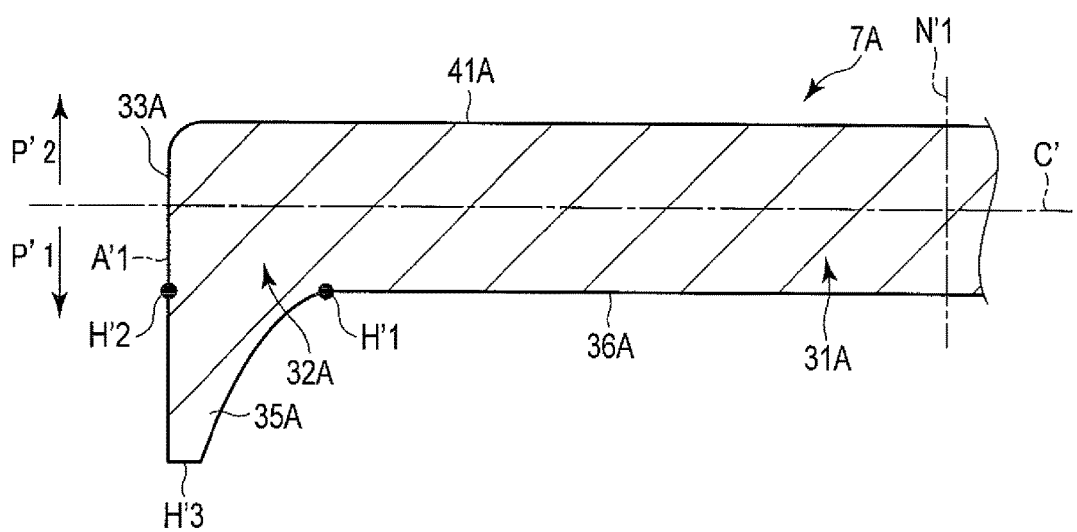
FIG. 5 is a cross-sectional view schematically showing a configuration of a distal portion of an ultrasonic probe according to a comparative example.

An ultrasonic probe 7A according to a comparative example of the embodiment is shown in FIG. 5. Like the ultrasonic probe 7 of the first embodiment, in the ultrasonic probe 7A of the comparative example, a hook 35A is provided in the distal treatment section 32A. The hook 35A protrudes in the first perpendicular direction (i.e., the direction indicated by arrow P'1 in FIG. 5), with the first base surface 36A being as a base surface. As in the first embodiment, in the ultrasonic probe 7A, a second base surface 41A facing the second perpendicular direction (the direction indicated by arrow P'2 in FIG. 5) is provided. Unlike the first embodiment, in the comparative example, a protrusion (42) is not provided. Therefore, the second base surface 41A extends toward the distal direction up to the distal surface 33A of the ultrasonic probe 7A.

When the ultrasonic probe 7A performs longitudinal vibration whose vibration direction is parallel to the longitudinal axis due to the ultrasonic vibration, a moment attributable to the shape of the hook is generated, with the hook proximal end H'1 (hook base section) of the hook 35A being as a center. Due to the generated moment, the hook 35A may swing, with the proximal end H'1 (hook root section) of the hook 35A as a center.

Figure 6:
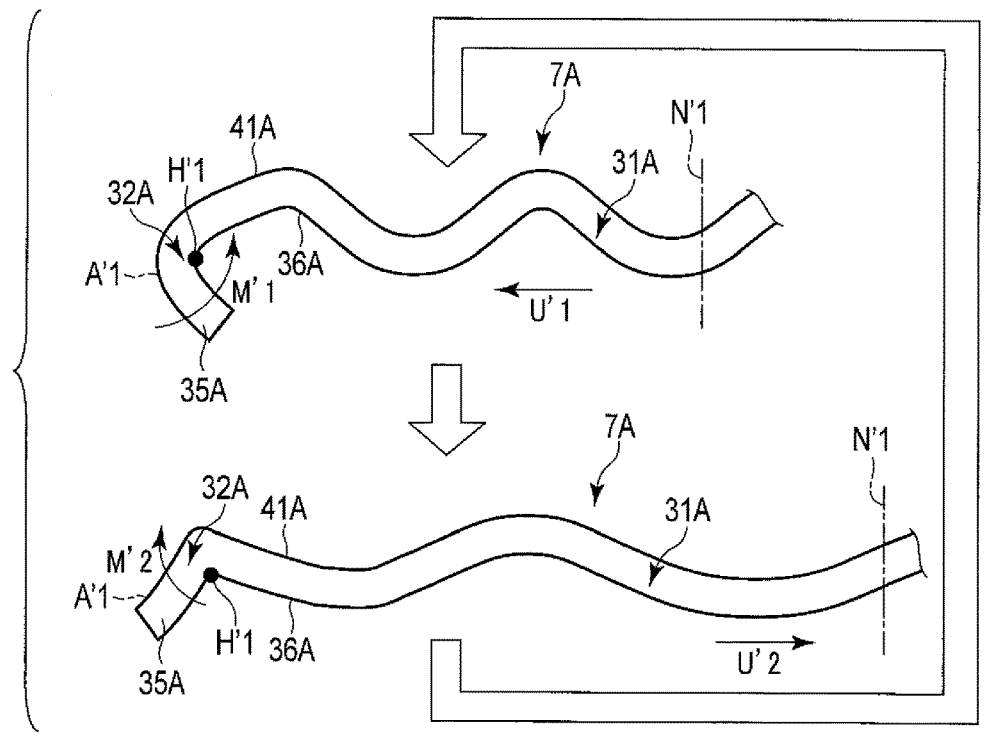
FIG. 6 is a schematic diagram illustrating how the ultrasonic probe of the comparative example vibrates when it is transmitting the ultrasonic vibration.

FIG. 6 is a diagram illustrating how the ultrasonic probe 7A of the comparative example vibrates when it is transmitting the ultrasonic vibration. Among the node position of the longitudinal vibration, the one which is located most distally is defined as a node position N'1. As shown in FIG. 6, when those portions of the ultrasonic probe 7A which are located on the distal direction side with respect to the node position N'1 undergo longitudinal vibration with the portions moving away from the node position N'1 (toward the distal direction) (as indicated by arrow U'1 shown in FIG. 6), a moment (first moment) M'1 is generated with the hook proximal end H'1 (hook root section) of the hook 35A being as a center. Due to the generated moment M'1, the hook 35A swings toward the proximal direction, with the hook proximal end H'1 of the hook 35A being as a center. On the other hand, when those portions of the ultrasonic probe 7A which are located on the distal direction side with respect to the node position N'1 undergo longitudinal vibration with the portions approaching to the node position N'1 (toward the proximal direction) (as indicated by arrow U'2 shown in FIG. 6), a moment (second moment) M'2 acting in the opposite direction of moment M'1 is generated with the hook proximal end H'1 (hook base section) of the hook 35A being as a center. Due to the generated moment M'2, the hook 35A swings toward the distal direction with the hook proximal end H'1 of the hook 35A being as a center.

The moments M'1 and M'2 that swing the hook 35A have an effect on those portions of the distal treatment section 32A which are other than the hook 35A (i.e., on the portions which are located on the second perpendicular direction side with respect to the hook 35A). Applied with moment M'1, those portions of the distal treatment section 32A which are other than the hook 35A move toward the second perpendicular direction. Applied with moment M'2, those portions of the distal treatment section 32A which are other than the hook 35A move toward the first perpendicular direction. Since moments M'1 and M'2 cause the distal treatment section 32A to move in the first perpendicular direction and the second perpendicular direction, a transverse vibration whose vibrating direction is perpendicular to the longitudinal direction C' (i.e. parallel to both the first and second perpendicular directions) is generated in the distal treatment section 32A. In addition, since moments M'1 and M'2 are exerted on those portions of the distal treatment section 32A which are other than the hook 35A, a torsional vibration may be generated around the longitudinal axis C, and a surface acoustic wave vibration wherein only the surface of the ultrasonic probe 7 vibrates is also generated. The vibrations other than the longitudinal vibration, including the transverse vibration, the torsional vibration and the surface acoustic wave vibration, will be referred to as inaccuracy vibrations. Inaccuracy vibrations caused by moments M'1 and M'2 are transmitted toward the proximal direction from the distal treatment section 32A. As a result, the entire ultrasonic probe 7A is subjected to the imprecise vibration, resulting in unstable vibration of the ultrasonic probe 7A.

In the present embodiment, the protrusion 42 protruding toward the second perpendicular direction is provided in the distal treatment section 32 of the ultrasonic probe 7. The protrusion 42 extends toward both the proximal direction and the distal direction from a reference position B0 located on the reference section Q0, which is perpendicular to longitudinal axis C and which passes through the hook proximal end H1 of the hook 35. The moment which swings the hook 35 is applied to the hook 35, with the hook proximal end H1 being as a center. Therefore, the moment which swings the hook 35 has an effect on the distal treatment section 32 in such a manner that the effect increases in the reference section Q0 including reference position B0 and in the neighborhood of the reference section Q0. In the present embodiment, the protrusion 42 extends in the longitudinal direction, passing the reference position B0 located on the reference section Q0. Therefore, the cross sectional area of the distal treatment section 32 perpendicular to the longitudinal axis C is large in the reference section Q0 and in the neighborhood of the reference section Q0. With this structure, the rigidity of the distal treatment section 32 is increased in the reference section Q0 and in the neighborhood of the reference section Q0, and those parts are strong against an external force (moment) applied from the direction perpendicular to the longitudinal direction C (from the direction traversing the longitudinal direction C). Therefore, even if the moments that swing the hook 35 are applied, those portions of the distal treatment section 32 which are other than the hook 35 (i.e., the portions which are located on the second perpendicular direction side with respect to the hook 35) are hard to move.

Figure 7:
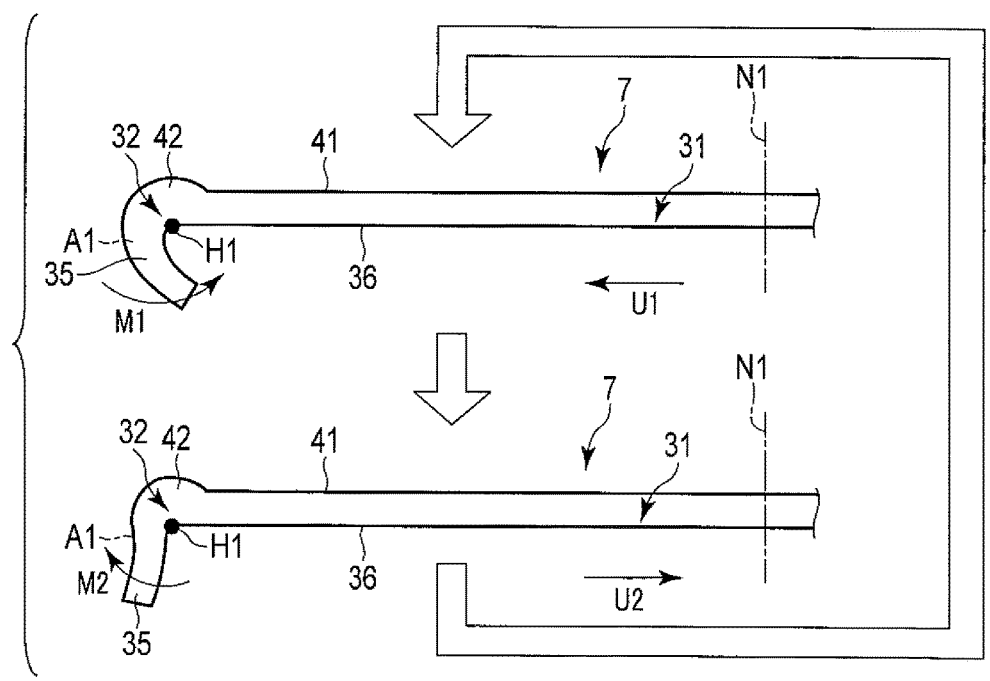
FIG. 7 is a schematic diagram illustrating how the ultrasonic probe of the first embodiment vibrates when it is transmitting the ultrasonic vibration.

FIG. 7 is a diagram illustrating how an ultrasonic probe 7 vibrates when it is transmitting the ultrasonic vibration. As shown in FIG. 7, when those portions of the ultrasonic probe 7 of the present embodiment which are located on the distal direction side with respect to node position N1 of the longitudinal vibration (i.e., the most distal node position) undergo longitudinal vibration with the portions moving away from the node position N1 (toward the distal direction) (as indicated by arrow U1 shown in FIG. 7), a moment (first moment) M1 is generated with the hook proximal end H1 (hook root section) of the hook 35 being as a center. Due to the generated moment M1, the hook 35 swings toward the proximal direction with the hook proximal end H1 being as a center. On the other hand, when those portions of the ultrasonic probe 7 which are located on the distal direction side with respect to the node position N1 undergo longitudinal vibration with the portions approaching to the node position N1 (toward the proximal direction) (as indicated by arrow U2 shown in FIG. 7), a moment (second moment) M2 acting in the opposite direction of moment M1 is generated with the hook proximal end H1 (hook base section) of the hook 35 being as a center. Due to the generated moment M2, the hook 35 swings toward the distal direction with the hook proximal end H1 being as a center.

Since the protrusion 42 is formed in the present embodiment, the rigidity of the distal treatment section 32 is increased in the reference section Q0 and in the neighborhood of the reference section Q0, and those parts are strong against an external force (moment) applied from the direction perpendicular to the longitudinal direction C (from the direction traversing the longitudinal direction C). Even if moment M1 is applied to those portions of the distal treatment section 32 which are other than the hook 35 (i.e., on the portions which are located on the second perpendicular direction side with respect to the hook 35), those portions of the distal treatment section which are other than the hook 35 do not move in the second perpendicular direction. Likewise, even if moment M2 is applied, those portions of the distal treatment section 32 which are other than the hook 35 do not move in the first perpendicular direction. Therefore, the transverse vibration due to the moments M1 and M2 which swing the hook 35 is not generated in the distal treatment section 32. Likewise, the torsional vibration or surface acoustic wave vibration which may be caused by moments M1 and M2 is not generated in the distal treatment section 32.

Since inaccuracy vibrations attributable to moments M1 and M2, such as transverse vibration and a torsional vibration, are reliably prevented from being generated in the distal treatment section 32, the ultrasonic probe 7 does not undergo inaccuracy vibrations. In the state where the ultrasonic vibration is being transmitted, therefore, the ultrasonic probe 7 performs the longitudinal vibration in a suitable manner, and the stable vibration of the ultrasonic probe 7 is ensured. As a result, the ultrasonic probe 7 enables reliable transmission of the ultrasonic vibration, and yet has sufficient strength against the ultrasonic vibration.

The protrusion 42 extends toward the proximal direction from reference position B0 located on the reference section Q0, which is perpendicular to longitudinal axis C and which passes through the hook proximal end H1, by the first extension dimension S1, which is more than half (L0/2) of the reference dimension L0 of the hook 35 (i.e., the hook base dimension). Also, the protrusion 42 extends toward the distal direction from reference position B0 located on the reference section Q0 by the second extension dimension S2, which is more than half (L0/2) of the reference dimension L0 of the hook 35. As can be seen from this, the protrusion 42 is provided in the range in which the effects of moments M1 and M2 that swing the hook 35 are large, i.e., the range determined by the reference dimension L0 with the hook proximal end H1 being as a central position in the longitudinal direction. With this structure, the rigidity is increased in the range determined by the reference dimension L0 with the hook proximal end H1 being as a central position in the longitudinal direction, and the strength against an external force (moment) applied from the direction perpendicular to (traversing to) the longitudinal direction C is enhanced in above range. As a result, even if the moments that swing the hook 35 are applied, the imprecise vibration is reliably prevented from being generated in those portions of the distal treatment section 32 which are other than the hook 35 (i.e., the portions which are located on the second perpendicular direction side with respect to the hook 35).

The second protrusion dimension (protrusion protruding dimension) R2 in the second perpendicular direction from the second base surface 41 (extension plane E2) to the protrusion protruding end T3 of the protrusion 42 is smaller than the first protrusion dimension (hook protruding dimension) R1 in the first perpendicular direction from the first base surface 36 (extension plane E1) to the hook protruding end H3 of the hook 35. Even though the protrusion 42 is provided in the distal treatment section 32, the dimension of the distal treatment section in the first perpendicular direction and the second perpendicular direction can be small. Even though the protrusion 42 is provided in the distal treatment section 32, the distal treatment section 32 (ultrasonic probe 7) can be small in size.

Since the protrusion 42 is provided with a proximal-side curved surface 48 and a distal-side curved surface 49, it does not have any angled portion on the outer surface. Even if the protrusion 42 comes into contact with a living tissue when the ultrasonic probe is vibrating, the living tissue is reliably kept from being damaged.

Modifications

Figure 8:
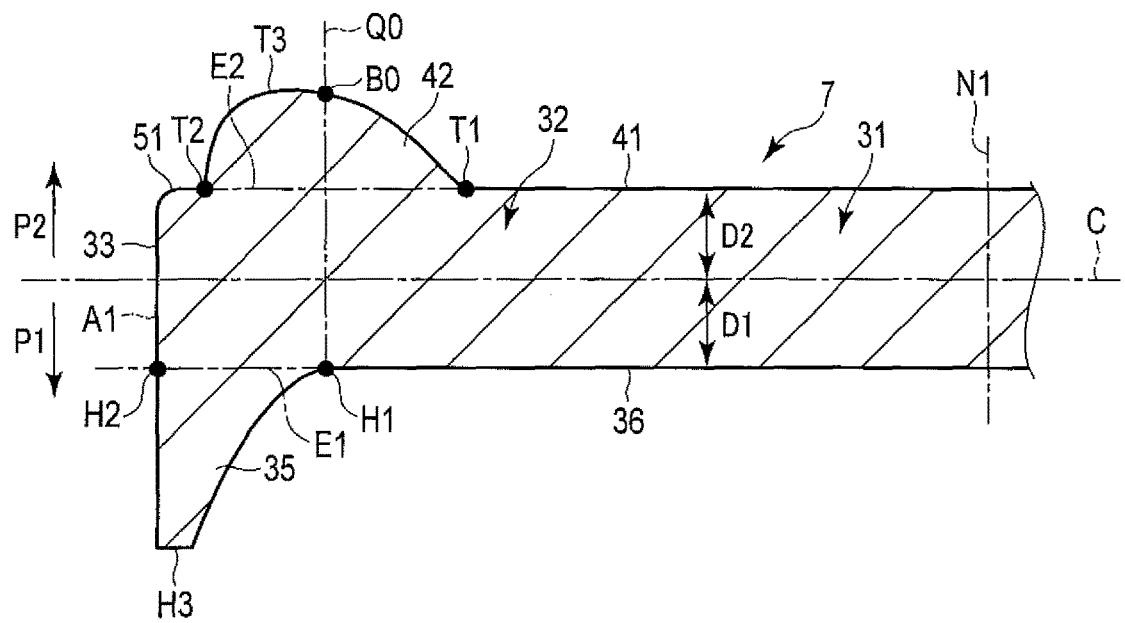
FIG. 8 is a cross-sectional view schematically showing a configuration of a distal portion of an ultrasonic probe according to a first modification.

In the first embodiment, the protrusion 42 forms part of the distal surface 33 of the ultrasonic probe 7. However, it is not limited. For example, an extension surface 51 may be provided on the distal direction side of the protrusion 42, as in the first modification shown in FIG. 8. The extension surface 51 extends toward the distal direction from the protrusion distal end T2 of the protrusion 42 up to the distal surface 33 of the ultrasonic probe 7. With this structure, the protrusion distal end T2 is a boundary position between the protrusion 42 and the extension surface 51. The extension surface 51 is directed in the second perpendicular direction. In the present modification, the extension surface 51 does not protrude from the second base surface 41 toward the second perpendicular direction.

In the present modification as well, the protrusion 42 extends through the reference position B0 located on the reference section Q0 which is perpendicular to longitudinal axis C and which passes through the hook proximal end H1 of the hook 35. In other words, the protrusion 42 extends toward the proximal direction and the distal direction from reference position B0.

Figure 9:
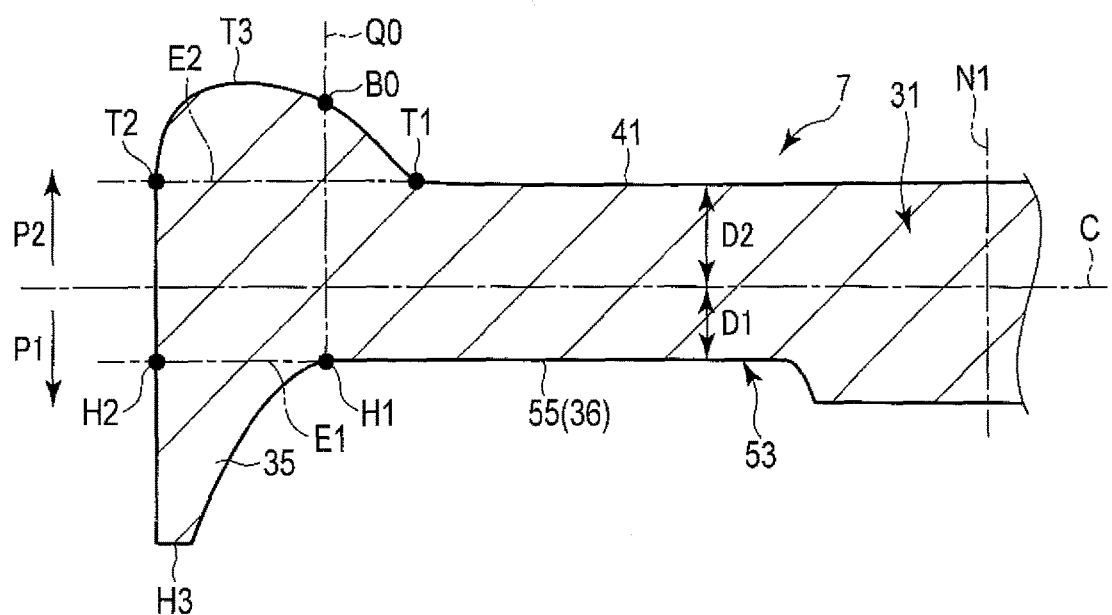
FIG. 9 is a cross-sectional view schematically showing a configuration of a distal portion of an ultrasonic probe according to a second modification.

In the first embodiment, the first base surface 36 extends through the outer surface of the probe main portion 31. However, it is not limited. For example, a concave surface 53 may be continuous between the outer surface of the probe main portion 31 and the hook 35 in the longitudinal direction, as in the second modification shown in FIG. 9. The concave surface 53 is concaved toward the second perpendicular direction relative to the outer surface of the probe main portion 31 and the hook 35. The concave surface 53 includes a concave bottom face 55 directed in the first perpendicular direction. The concave bottom face 55 extends toward the proximal direction from the hook proximal end H1 of the hook 35.

In the present modification, the entire concave bottom face 55 constitutes the first base surface 36. Therefore, the distance D1 (the first surface distance) by which the concave bottom face (the first base surface 36) is away from the longitudinal axis C toward the first perpendicular direction is constant (uniform) within a predetermined dimensional range over the entire length in the longitudinal direction.

In the present modification as well, the protrusion 42 extends through the reference position B0 located on the reference section Q0 which is perpendicular to longitudinal axis C and which passes through the hook proximal end H1 of the hook 35. In other words, the protrusion 42 extends in both the proximal direction and the distal direction from reference position B0.

The ultrasonic probe (7) according to the above embodiments etc. (except the comparative example) includes: a probe main portion (31) extending along a longitudinal axis (C) and configured to transmit an ultrasonic vibration from a proximal direction (C2) toward a distal direction (C1); and a hook (35) provided on the distal direction (C1) side with respect to the probe main portion (31) and curved toward a first perpendicular direction (P1) relative to the probe main portion (31). The hook (35) forms a part of the distal surface (33) of the ultrasonic probe (7). A first base surface (36) extends toward the proximal direction (C2) from a hook proximal end (H1), which is the proximal end position of the hook (35). The first base surface (36) is the base surface of the hook (35) protruding toward a first perpendicular direction (P1). The distance (D1) by which the first base surface (36) is away from the longitudinal axis (C) in the first perpendicular direction (P1) is constant (uniform) within a predetermined dimensional range over the entire length of the first base surface in the longitudinal direction. A protrusion (42) is continuous with the distal direction (C1) side of a second base surface (41) which is directed in a second perpendicular direction (P2). The protrusion (42) protrudes toward the second perpendicular direction (P2), with the second base surface (41) being as a base surface. The protrusion (42) extends toward both the proximal direction (C2) and the distal direction (C1) from a reference position (B0) located on the reference section (Q0), which is perpendicular to longitudinal axis (C) and which passes through the hook proximal end (H1) of the hook (35).

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic probe having a longitudinal axis, the ultrasonic probe comprising:
    a probe main body extending along the longitudinal axis, and configured to transmit an ultrasonic vibration from a proximal direction toward a distal direction;
    a hook provided distally of the probe main body, and curved relative to the probe main body in a first perpendicular direction, which is perpendicular to the longitudinal axis, the hook forming a part of a distal surface of the ultrasonic probe, the distal surface forming a most-distal point of the ultrasonic probe and facing the distal direction;
    a first base surface
        facing the first perpendicular direction on an outer surface of the probe main body,
        serving as a first base plane of the hook protruding toward the first perpendicular direction,
        extending toward the proximal direction from a most-proximal point of the hook, and,
        spaced from the longitudinal axis toward the first perpendicular direction by a distance which is constant at a predetermined dimension over an entire length of the first base surface in a longitudinal direction along the longitudinal axis,
    the most-proximal point of the hook being located at a boundary between the first base surface and the hook,
    a first extension plane, which is an extension of the first base surface in the distal direction from the most-proximal point of the hook, forming a root of the hook and passing through a most-distal point of the hook,
    the most-distal point of the hook being located on the distal surface of the ultrasonic probe;
    a second base surface facing a second perpendicular direction opposite to the first perpendicular direction on an outer surface of the probe main body; and a protrusion continuous with a distal end of the second base surface, and protruding toward the second perpendicular direction with the second base surface being a second base plane, a most-proximal point of the protrusion being located at a boundary between the second base surface and the protrusion, a second extension plane, which is an extension of the second base surface in the distal direction from the most-proximal point of the protrusion, forming a root of the protrusion and passing through a most-distal point of the protrusion, the protrusion extending toward both the proximal direction and the distal direction from a reference position located on a section, which passes through the most-proximal point of the hook and which is perpendicular to the longitudinal axis, wherein when a dimension between the most-distal point of the hook and the most-proximal point of the hook in the longitudinal direction is defined as a reference dimension, the protrusion extends from the reference position to the most-proximal point of the protrusion toward the proximal direction by a first extension dimension which is more than one half of the reference dimension, and the protrusion extends from the reference position to the most-distal point of the protrusion toward the distal direction by a second extension dimension which is more than one half of the reference dimension.

2. The ultrasonic probe according to claim 1, wherein a first protruding dimension by which the hook protrudes from the first base surface to a point displaced most laterally in the first perpendicular direction in the hook is larger than a second protruding dimension by which the protrusion protrudes from the second base surface to a point displaced most laterally in the second perpendicular direction in the protrusion.

3. The ultrasonic probe according to claim 1, further comprising:

a concave surface provided on the outer surface of the probe main body, and being concave in the second perpendicular direction, wherein the concave surface includes a concave bottom surface facing the first perpendicular direction, and the first base surface extends on the concave bottom surface.

4. The ultrasonic probe according to claim 1, wherein a distance by which the second base surface is away from the longitudinal axis in the second perpendicular direction is constant at a predetermined dimension over an entire length of the second base surface in the longitudinal direction.

5. The ultrasonic probe according to claim 1, wherein the protrusion forms a part of the distal surface of the ultrasonic probe.

6. The ultrasonic probe according to claim 1, wherein the protrusion includes:

a proximal-side protrusion surface extending toward the second perpendicular direction from a boundary position between the second base surface and the protrusion, and facing the proximal direction;

a distal-side protrusion surface extending toward the second perpendicular direction, and facing the distal direction;

a protrusion end surface that forms a point displaced most laterally in the second perpendicular direction in the protrusion;

a proximal-side curved surface being continuous between the proximal-side protrusion surface and the protrusion end surface; and a distal-side curved surface being continuous between the distal-side protrusion surface and the protrusion end surface.

7. An ultrasonic treatment apparatus comprising:

an ultrasonic probe according to claim 1;

a vibration generator supplied with ultrasonic generating electric power so as to generate the ultrasonic vibration to be transmitted to the ultrasonic probe.

* * * * *